United States Patent [19]

Chen

[11] Patent Number: 4,505,275
[45] Date of Patent: Mar. 19, 1985

[54] TREATMENT METHOD AND INSTRUMENTATION SYSTEM

[76] Inventor: Wu Chen, 26 W. Ridge Pike, Royersford, Pa. 19468

[21] Appl. No.: 338,066

[22] Filed: Jan. 8, 1982

Related U.S. Application Data

[63] Continuation-in-part of Ser. No. 833,562, Sep. 15, 1977, abandoned, and a continuation-in-part of Ser. No. 17,846, Mar. 6, 1979, abandoned.

[51] Int. Cl.³ ............................................. A61N 1/36
[52] U.S. Cl. .................................................. 128/421
[58] Field of Search ............... 128/419 R, 420 R, 421, 128/423 R, 643, 741

[56] References Cited

U.S. PATENT DOCUMENTS

| | | | |
|---|---|---|---|
| 2,808,826 | 10/1967 | Reiner et al. | 128/741 |
| 3,718,132 | 2/1973 | Holt et al. | 128/421 |
| 3,727,616 | 4/1973 | Lenzkes | 128/422 |
| 3,810,457 | 5/1974 | Boticher et al. | 128/741 |
| 3,958,564 | 5/1976 | Langguth | 128/643 |
| 4,014,323 | 5/1977 | Gilmer et al. | 128/422 |

*Primary Examiner*—William E. Kamm

[57] ABSTRACT

The method comprises steps of applying a treatment characterized by parameters at least one of which has a relatively broad range of controllable values, of detecting the response from the treatment object, of selecting a subset of parameters, of selecting the proper magnitude of those selected parameters, of prescribing the selected parameters at the selected range of values for subsequent use of the treatment object, and of defining an instrument unit having the prescribed parameters and range of values for the exclusive use of the treatment object.

The instrumentation system comprises a clinical unit which has parameters at least one of which has a range of controllable parameters for use primarily in the clinic to cover a large variety of cases, and a private treatment unit which has a selected subset of parameters from those of the set of parameters of clinical unit and each of the selected parameters has a properly selected value or range of values. The selection of the parameters and their respective values is based on diagnostic procedure performed with the clinical unit whereby detectable result, if any, is observed from the clinical treatment. The instrumentation system may incorporate means for generating a subjective referencing stimulation, means for generating an indicator stimulation, means for generating a time-sequence programming in applying the treatment, and electrode means with improved applicational mobility. A method of quantitative measurement of the object's response is disclosed and implemented.

17 Claims, 16 Drawing Figures

| A<br>CLINICAL INSTRUMENT | B<br>PERSONAL INSTRUMENT | C<br>ELECTRODES | | |
|---|---|---|---|---|
| [3-1] AMPLITUDE<br>[3-2] FREQUENCY<br>[3-3] WAVEFORM (OPTIONAL)<br>(3-4) PULSE WIDTH (OPTIONAL)<br>[3-5] MODULATION (OPTIONAL)<br>[3-6] POLARITY (OPTIONAL)<br>[3-0] | [3-10] SAME AS THE CLINICAL UNIT [3-0] | [3-12] ATTACHABLE OR IMPLANTABLE ELECTRODES | I. PRIOR-ART INSTRUMENTATION | INSTRUMENTATION MADE POSSIBLE BY THE PRESENT INVENTION |
| [3-7] SUBJECTIVE REFERENCING (OPTIONAL)<br>[3-8] INDICATOR STIMULATION (OPTIONAL)<br>[3-9] TREATMENT-PATTERN PROGRAMMING (OPTIONAL) | [3-11] DIFFERENT FROM THE CLINICAL UNIT, HAVING SELECTED FEATURE PARAMETERS ONLY | [3-13] SEGMENT-SELECT ELECTRODE<br>[3-14] DOUBLE-CUP SUCTION ELECTRODE | II EMBODIMENT OF THIS INVENTION | |

FIGURE 9A  PARAMETERS OF THE CLINICAL UNIT

FIGURE 9B  CLINICAL TREATMENT AND PRESCRIPTION PROCESS, PATIENT X

FIGURE 9C  PRESCRIPTION AND PARAMETERS OF INDIVIDUAL TREATMENT UNIT, PATIENT X

FIGURE 9D  PRESCRIPTION AND PARAMETERS OF INDIVIDUAL TREATMENT UNIT, PATIENT Y

TREATMENT METHOD AND INSTRUMENTATION SYSTEM

BACKGROUND OF THE INVENTION

This is a continuation in part of applications Ser. No. 833,562 filed Sept. 15, 1977, and Ser. No. 017,846, filed Mar. 6, 1979, both now abandoned.

In the field of applying outside stimuli to a biological body for a desired effect, such as the application of electricity to the nerve for pain relief or for muscular rehabilitation, the prior-art instrumentation consists of a single package of electronics to generate the stimulating electricity, together with controls for the electrical parameters, and the interfacing means for applying the stimulation to the desired location in or on the body.

Such an approach in instrumentation is similar to that of patent medicine in the field of medication. The manufacturer puts into the package whatever he thinks is good for the cure and lets the users try it out. Different manufacturers have varied claims of features, but there is no systematic way of comparing these features. Since the method of treatment that is open to the practitioner is as a rule limited by the instrument available to him, therefore the prior-art treatment method is also akin to that for the patent medicine. The practitioner selects one make of instrument, either by recommendation or from his own experience, and tries it on the object. If the desired effect cannot be obtained, he either switches to another make of instrument or discontinues the treatment. If there is indication that the desired effect can be achieved, then he continues to treat the object either in his clinic or provides the patient with a personal unit for use outside the clinic. The same type of unit is used both clinically and personally.

The above described prior-art method and instrumentation, while time honored and proven effective, have shortcomings in two important aspects which prevent the treatment from realizing its full potential.

Firstly, the prior-art instrumentation does not have sufficient capability to deal with the delicate biological and interfacing aspects of this type of treatment. The response from the biological elements in a living body to an electrical stimulation is very subjective. The response or non-response, the threshold of the response, the ceiling of tolerance to the stimulation, and the ability to consciously recognize the response, vary greatly among the different types of biological elements. Even for the same type of element, they can still differ at different locations of the body, for each human being or animal, or under different physiological or pathological conditions. It is further complicated by the fact that certain desired types of response require very strong stimulation bordering the limit of tolerance, while others may need only weak stimulation below conscious recognition.

Due to the above mentioned multifacet and wide-ranging subjectivity of response to stimulation, there is a need for a subjective calibration to quantitatively gauge the dosage of the stimulation with due regard to the individuality of the biological element and the physiological and pathological conditions.

In the prior-art instrumentation, the importance of a subjective calibration has not been recognized and there has been no implementation toward this end. In general, the prior-art instruments are calibrated in arbitrary scale such as from 0 to 10 and the representation of the scale differs from manufacturer to manufacturer. Furthermore, it bears no relation to the subjectivity phenomena. Some instruments are calibrated in scientific terms such as volt, ampere, hertz, etc. However, due to the complicated overlapping caused by the subjectivity in response, what is effective to one patient may not necessarily be effective to another, these scientific calibrations, while having meaning on a macroscopic scale from a statistical viewpoint, have little meaning to an individual unless a quantitative subjective scale can also be translated to fit that individual.

In the prior art, any subjective gauging of the stimulation comes from the conscious recognition of the object who in turn verbally communicates to the practitioner. This at best is a qualitative indication and it is not possible to put into quantitative terms for precise control of the stimulation. Under certain conditions, the stimulation is not even recognizable to the object.

Thus the inability to subjectively gauge the dosage is one deficiency in the prior art which prevents the medical treatment of electrical stimulation from realizing its full potential. A second deficiency stems from the fact that although in some cases the desired response from the stimulation may be evident within a short time, yet it is also often that the response is not so evident and may not be recognized by the patient within a reasonable time. Again, the prior art depends on the conscious recognition of the response of the patient and is subject to the drawback previously discussed. Consequently there is a need for a method to more properly gauge the effectiveness of the stimulation.

There is still another deficiency in the prior art, which arises from the fact that biological elements inside the body are delicately interwoven. Unless surgery is performed, there is no way to separate one element from another. On the other hand, the applicator electrode which conducts the stimulation to the body has influence over an area which encompasses many biological elements. Due to the subjectivity phenomena discussed before, the responses to the stimulation are not the same by these various elements. Some of the responses may even be antagonizing to the desired response. Therefore it is highly desirable that the applicator electrode can do as much as possible in selecting the right biological element for stimulation and bearing the others alone, at least those that would respond undesirably. The prior art not only makes no conscious effort toward this goal, but also, on account of the method used in attaching the electrodes to the body, suffers from the lack of mobility once they have been attached. Such a lack of mobility is a great handicap at the initial diagnostic exploration to locate the right place to apply the stimulation.

Besides the deficiencies in the prior-art method and instrumentation as above discussed, the second aspect that severely limits the efficacy of the medical treatment by electrical stimulation stems from a paradox inherent in the patent-medicine approach which it has evolved into. In the pattern of patent medicine, the prior art offers a single package of electronics to do all the jobs under all occasions and with insufficient provisions to meet the wide-ranging requirements that will be encountered. While trial and error is a time-honored method in medicine and patent medicine has proven its effectiveness in many areas, its adaptation to the medical treatment by stimulation needs a careful re-examination.

In the treatment by stimulation, there are two major uses of the instrumentation that go hand in hand. It may be intended for general use by a practioner to treat an indefinite number of patients, operated by personnel with specialized knowledge and experience in the field. In this specification and the subsequent claims of this invention, instrument for the above use is defined as the clinical treating unit or clinical unit, although its use may not be confined in a clinic. The second use of the instrumentation is that when the object needs frequent treatments or treatments for a long period, an individual treating unit for that one object is needed. In this latter case, the instrument is intended for private use of a single object whose condition has been explored by the practioner and the treatment requirement is pretty well defined and who has little or no knowledge to operate the instrument.

The requirements for these two uses are quite opposite to each other. For general use by a practioner, it is desirable that, the instrumentation has comprehensive provisions, precise calibrations, and special means to allow the practitioner to determine the response of the object. The cost, size, and simplicity of operation are not the primary considerations. On the other hand, for personal use, the instrumentation needs only to have whatever provision as required by that one particular object, and the cost, size, and simplicity in operation all become important considerations.

Consequently, it is easy to understand that the instrumentation that is comprehensive and precise enough for general use would be too expensive, too bulky, and too complicated to operate for individual use. On the other hand, the instrumentation that satisfies the requirements for individual use cannot be versatile and precise enough for general applications. Any instrument seeking to encompass both sides of this paradox is necessarily making compromise in one way or the other, and ends up in compromising the efficacy of the treatment.

The prior art has not come to the recognition of this paradox and is contented in getting whatever that can come out of the single-package, patent-medicine approach. However, after a careful examination of the deficiencies of the prior-art method and instrumentation and of the inherent paradox of the patent-medicine approach as applied to the field of treatment by stimulation, it becomes clear that for the same reason that medication has evolved from the stage of trial and error and patent medicine to include diagnostic-prescriptional medication, the stimulation treatment should also evolve into a stage including the diagnostic-prescriptional option for better results.

SUMMARY OF THE INVENTION

It it the primary object of the present invention to improve the method and instruments for applying outside stimuli to a biological body for a desired effect.

It is further object of the present invention to provide improved method and instrumentation to usher in the medical treatment of stimulation into an era in which the option of diagnostic-prescriptional precision and is available to the practitioners.

It is another object of the present invention to provide method and instrumantation to remedy the deficiencies and to resolve the paradox of the prior art.

The novel features considered characteristic of this invention are set forth with particularity in the appended claims. The invention itself, both as to its method and the instrumentation essential to support the method, as well as additional objects and advantages thereof, will best be understood from the subsequent detailed description when read in connection of the accompanying drawings disclosing by way of examples. a preferred embodiment of the invention.

DETAILED DESCRIPTION

Figure 1:
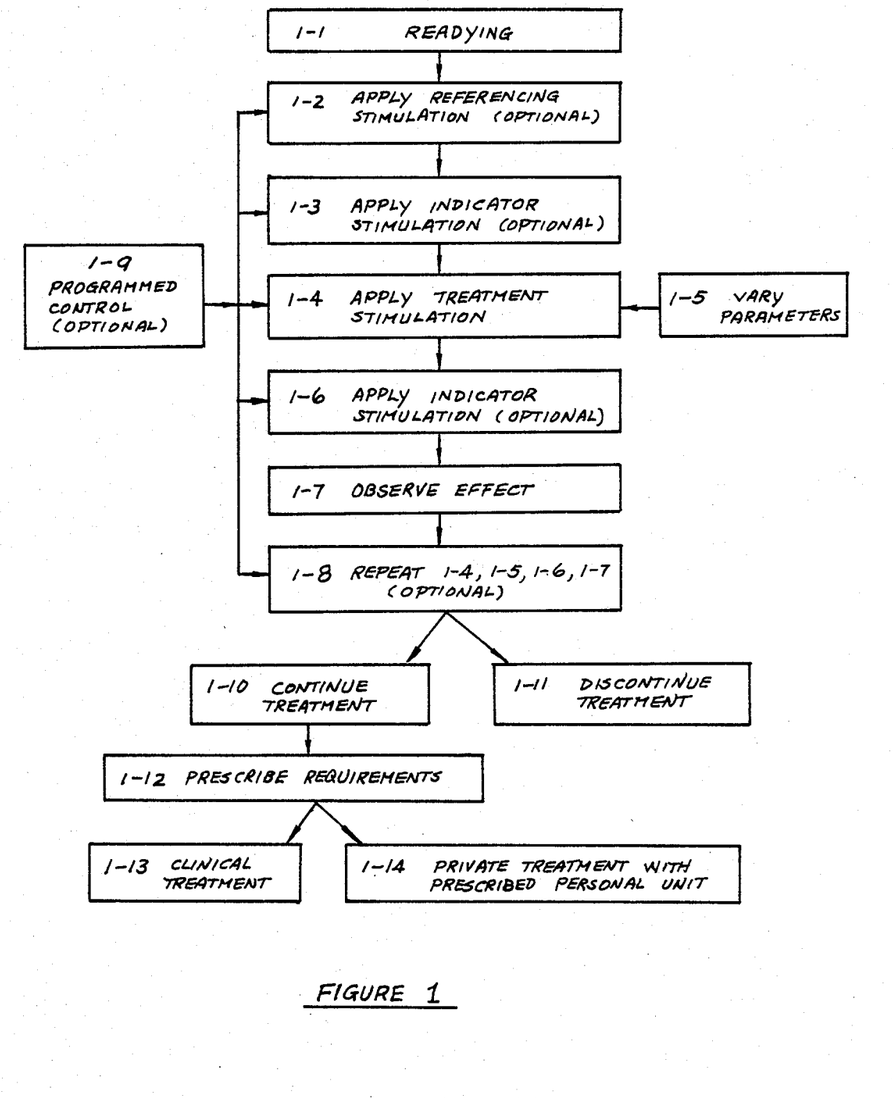
FIG. 1 is a flowchart showing by way of example the essential operational procedure of the method of this invention.
Figure 2:
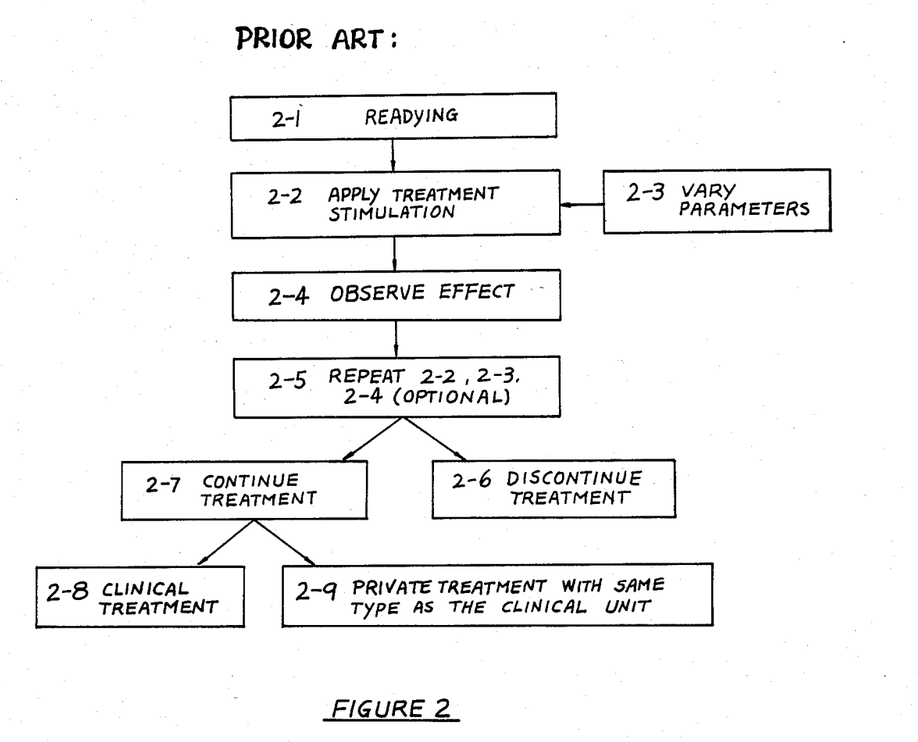
FIG. 2 is a flowchart showing the essential operational procedure of the prior art.

FIG. 1 is a flowchart depicting by way of example a preferred embodiment of the present invention in stimulation treatment. FIG. 2 is a flowchart depicting the prior-art method in this field. By comparing the procedures in FIG. 1 to those in FIG. 2, the novel improvements of the present invention over the prior art can also be observed.

Let us first start from FIG. 2 which depicts the essential procedural steps of the prior art.

2-1 represents the step to make ready for application of the treatment stimulation. In the case where the stimulation is externally applied, this preliminary preparation would include the applying of material for increasing the conducting efficiency of the stimulating electricity, such as water or conductive gel; the placing of the interfacing electrode to the location intended for applying the stimulation; and the fastening of the electrodes with adhesive tapes or bandages. In the case where the stimulation is applied internally, surgical procedure would instead be performed.

2-2 represents the activation of the instrument that supplies the stimulation. 2-3 represents the varying of the parameters of the stimulation as provided by the instrument. 2-4 represents the observing of the effect of the stimulation on the patient based upon the feeling of the patient and the experience of the practitioner. 2-5 represents the repeating of procedures 2-3 and 2-4 as many times as deemed desirable by the practitioner. 2-6 represents the decision to discontinue the treatment when there is no indication of the desired effect. 2-7 represents the decision to continue treatment when there is indication of the desired effect. 2-8 represents that further treatment would be conducted in the clinic using the same type of instrument. 2-9 represents personal treatment away from the clinic using the same type of instrument.

After noting the essential procedure in the prior art, we now move to describe the novel improvements from the present invention in connection of FIG. 1.

In the readying procedure 1-1, the present invention has an option of using the prior-art procedure as described in 2-1, or using the mobility-oriented or selectivity oriented electrodes, which will be fully described in connection with FIGS. 7A,7B,8A to 8C to more properly select the location for applying the stimulation. With these novel electrodes, the location for stimulation can be changed very conveniently during the later steps in the treatment procedure and therefore the change of location can also be included in procedure 1-5 in the same sense as the change of the electrical parameters.

Subsequently in procedure 1-2, which is devoid of in the prior art, effort is made to determine the subjective threshold on the location of the treatment stimulation or on other appropriate locations, so that the parameters of the treatment stimulation are adjusted with due consideration to the subjectivity of the individual patient. The details of this procedure are described in connection with 3-7, 4-2, 5-1 and 5-5.

In order to obtain quantitative measure on the effect of the treatment stimulation during and after the treatment, another novel procedure is incorporated which is also lacking in the prior art. This is the option in step 1-3 to apply the indicator stimulation, which is described in connection with 3-8 and illustrated with examples in connection with 4-3, 5-2, 5-4, and 5-6. By applying this procedure before the treatment stimulation of step 1-4 and repeating at programmed time intervals, it is now possible for the first time to gauge the effect of the treatment quantitatively as the treatment progresses and at the end of the treatment.

In the procedure 1-4, treatment stimulation is applied. During this time, the electrical parameters and also the location of the stimulation are adjusted as depicted in 1-5 with due consideration from the previous steps 1-1, 1-2, and 1-3.

After a proper time interval, the indicator stimulation is again applied in procedure 1-6 to gauge the extent and degree of the effect from the treatment stimulation. Other observations as those used in the prior art, i.e. step 2-4, are retained in procedure 1-7 along with the result from 1-6, for deciding the next step of the treatment. Procedures 1-4 to 1-7 may be repeated as many times as deemed appropriate, as indicated in procedure 1-8. During the repeat, the parameters and the electrode locations may be systematically varied if so desired, as depicted in 1-9.

The time sequence and the spatial pattern of the application of the three types of stimulations, i.e. the reference stimulation, the indicator stimulation, and the treatment stimulation, may be controlled by the programming procedure 1-9. Included in it also are the duration of each stimulation and the non-stimulating dead time between subsequent stimulations. This procedure 1-9 is also devoid in the prior art.

After sufficient information has been gathered from the treatment-observation cycles, a decision would be made at the end of procedure 1-8 whether the treatment is worth continuing. Step 1-11 would be taken to discontinue if there is no sign that the treatment would lead to the desired effect. Step 1-12 would be taken if there would be evidence that the desired effect would be possible. In the latter case, 1-12 represents that the electrical parameters, the range of values of these parameters, the required controls, the size and shape of the electrodes, and the locations for applying the stimulation, are decided and prescribed for that patient.

Future treatment may be carried out with the same clinical unit, as signified in 1-13, or with a personal unit made to the prescribed requirements from 1-12, as signified in 1-14.

Figure 3:
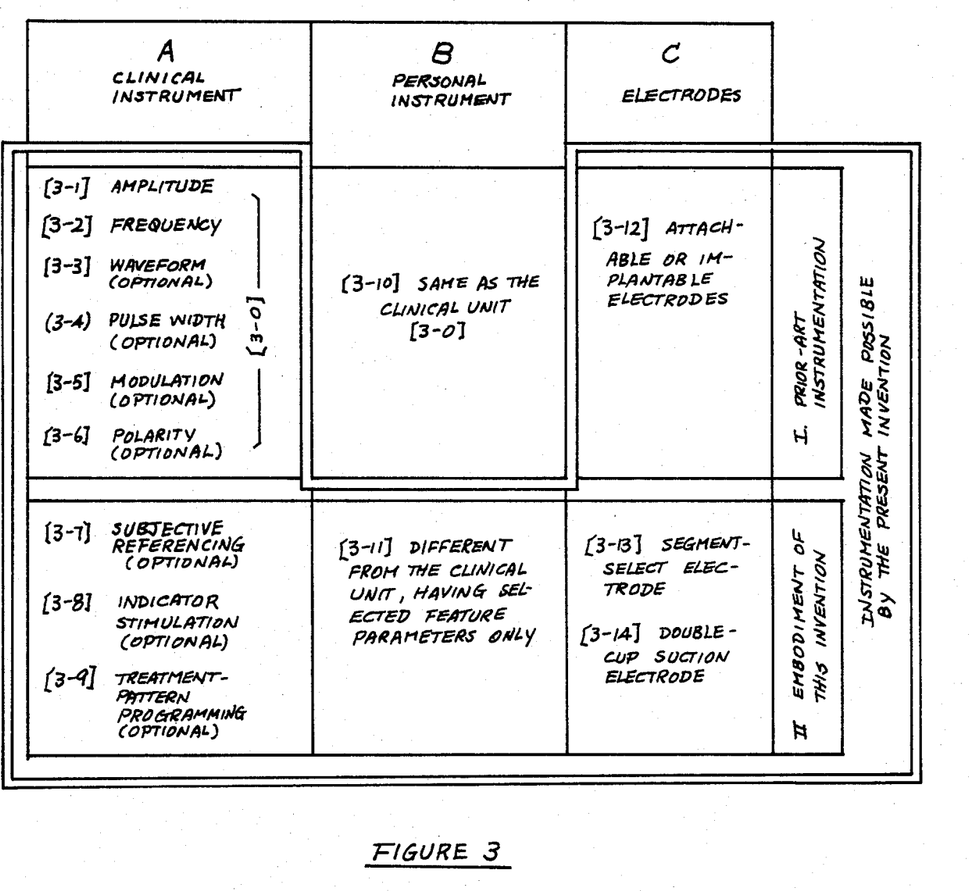
FIG. 3 is a listing diagram showing the parameters and components in the instrumentation of the prior art and the novel addition from the present invention.

The components of the instrumentation in both the prior art and in the present invention are listed semi-diagramatically in FIG. 3. It also purports to show those components that are in common with the prior art and those that are the novel features of the present invention.

The diagram of FIG. 3 has three columns designated as A, B, and C, and two rows designated as I and II. Column A tabulates the parameters and respective controls for the stimulation generating means of the instrumentation for clinical use which will deal with an unlimited number of patients. Column B tabulates the parameters and respective controls for an optional part of the instrumentation for use by a specified number of patients, usually one. Column C tabulates the available applicator means of the instrumentation. Parameters and features tabulated in Row I are those from the prior art. Row II tabulates the novel features of the present invention.

The treatment stimulation generating means 3-0 comprises one or more of the parameters with respective controls 3-1 to 3-6, which are public knowledge in the art. Of these six parameters, the amplitude 3-1 and the frequency 3-2 are more fundamental to the instrumentation and most frequently included except under very special situations. The inclusion of waveform 3-3, pulse width 3-4, modulating envelope 3-5, and polarity of pulse 3-6 as controllable parameters is optional in the prior art.

The parameters: subjective reference 3-7, indicator stimulation 3-8, and treatment pattern programing 3-9, are novel features of the present invention to add to the embodiment of the clinical part of the instrumentation. The subjective reference stimulation 3-7 is for establishing a referencing base level to the treatment dosage in accordance with the subjectivity of the individual patient. The nature of individual subjectivity has been discussed in a preceeding part of this application as a background of the invention. The idea behind this novel feature is a simple one. It is used to establish the threshold level of the patient while he is in his original condition before the treatment. Once such a base level is established, the relevant parameters for the stimulation are identified and adjusted in relative terms in regard to this referencing level. For instance, if the subjective reference is in terms of the amplitude 3-1, then the referencing base level is the stimulating current from which the patient barely feels the presence of the stimulation, and the stimulating dosage used for the treatment would be in terms of the ratio or the difference of this base level.

From this novel method of instituting an individual referencing base level and then referring to the treatment dosage in terms of ratio or difference to it, the stimulation can be administered in accordance with the individual condition of the patient in question. Whether it is to be over-stimulation above the base level or under-stimulation below the base level is administered by the subjective scale of that patient. The degree of over-stimulation or under-stimulation is put into precise and unambiguous terms, i.e. 150% base level, 50% base level, etc.

The subjective reference stimulation may be applied to the same location as the treatment stimulation, or it may be applied to other locations as deemed proper.

The base level as determined from the referencing stimulation can also be used as an index to the patient's condition, either as comparison means to a statistical model over a larger number of patients, or as a progress indicator in the treatment history if its long-term variation can be properly interpretated.

The subjective reference stimulation 3-7 has the following essential characteristics:
  a. At least one shot of stimulation
  b. It may be electrical or any other stimulating form which can provide a detectable threshold and deemed appropriate to the case at hand, such as force, pressure, heat, light, color, noise, etc.
  c. It may be applied either to the same location as the treatment stimulation, or to other locations as deemed appropriate.
  d. More than one type of stimulation on more than one location may be used.
  e. The electrical form of referencing stimulation may be in terms of amplitude, the base level would then be in volts, milliamperes, or micro-coulombs, at which the individual patient just begins to feel the presence of the stimulation. Or it may in terms of frequency, then the base level would be the largest number of pulses per unit time, which the individual patient is able to distinguish and count.
  f. The subjective reference stimulation is intended to applied to the individual patient in his original state of condition before each treatment. During each treatment, if it is to be applied in a repeated manner in order to adjust toward the threshold base level, the time interval between each application should be long enough so that the subsequent application would be free from the cumulative effect of prior applications.
  g. The patient's threshold of response may be determined from his sensory recognition or from other detectable response such as the change in the rate of his heart beat or in the body temperature.

Examples of the waveform of the referencing stimulation is shown as 5-1 and 5-5 in FIGS. 5A and 5B respectively and is further described in connection with these two figures. Example of means to generate the referencing stimulation is illustrated in connection with FIG. 6A, in which electrical stimulation is intended. Other suitable waveforms may be also used.

The indicator stimulation 3-8 purports to provide the indication on the short-term effect of the stimulation, which, when compiled over a period of time, would also give the trend of the long-term effect. It has the following essential characteristics:
  a. At least one group of shots of stimulation comprising two or more shots each having a predetermined ratio or difference among one another.
  b. When the indicator stimulation is programmed more than once in the treatment, the number of shots and the ratio of value between shots may remain unchanged or may be altered at each occurrence in a manner unknown to the patient but known to the practitioner in order to minimize any psychological suggestive effect on the part of the patient.
  c. It may be in electrical or other forms of stimulation as discussed in connection with the referencing stimulation 3-7.
  d. It is preferably calibrated in terms of a ratio or difference to the subjective base level as determined from the referencing stimulation 3-7, although other options can be used.
  e. When it is programmed to occur during or after the treatment stimulation, there should be sufficient time seperation so that short-term transient effect of the treatment stimulation will fade away before the application of the indicator stimulation.
  f. Similar to the reference stimulation 3-8, one or more indicator stimulations of the same form or different forms may be applied to one or more locations.

Figure 5A:
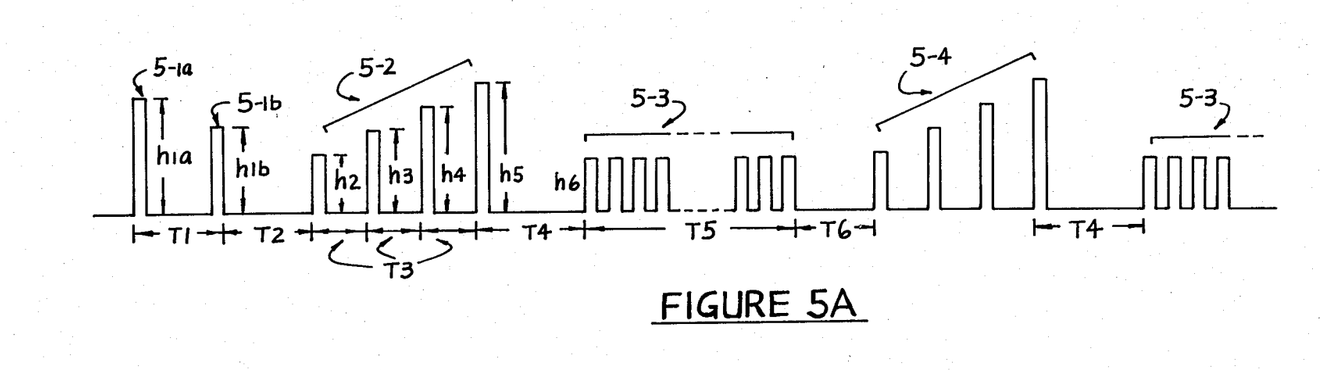
FIGS. 5A and 5B show examples of waveform of the novel function of the present invention.
Figure 5B:
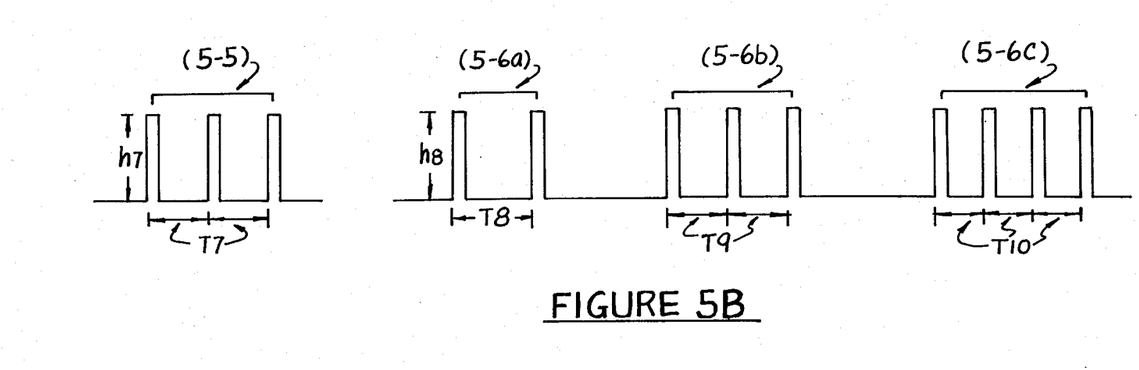

The way this novel feature of indicator stimulation works can best be explained with an example in its simpler form as depicted 5-2 and 5-4 in FIG. 5A. The first group of indicator pulses 5-2 has four shots of pulses having respective amplitudes $h_2$, $h_3$, $h_4$, and $h_5$, each being larger than the preceeding one by a known amount. Let $h_1$ be the base level of the object which has been determined by applying the referencing stimulation previously. The response from the object is only as having three pulses because the magnitude $h_2$ of the first pulse is below threshold level. Suppose that after being treated with the treatment stimulation 5-3, response from the object is detected as having only two pulses in the indicator group 5-4, then it would mean that the treatment stimulation 5-3 does produce some biological effect to that object as reflected in the change to a higher threshold upon which the second pulse having a magnitude $h_3$ is not responded. The proper interpretation of this effect would be the judgment of the practitioner. Similarly, if the object responds to all four pulses in the indicator group 5-4, then it would mean that the treatment stimulation has an effect on him in another direction. On the other hand, if the object's response would still be three pulses, then it would mean that either the treatment stimulation has no effect on him, or the effect is too small to be recognized. Continued cyclic application of the treatment stimulation and the indicator stimulation for a reasonable number of times would further differentiate the last mentioned two possibilities.

The above example demonstrates another element of the present invention, which uses physical stimulation in electrical, thermal, optical or mechanical form arranged in a manner capable of inducing a quantizable response in discrete levels from the treatment object. This quantizable response can be detected by sensory recognition or by a suitable device. It provides a quantitative measure on the effect of the treatment stimulation and precise and unambiguous communication between the patient and the practitioner. The practitioner is now able to record and interpret the patient's response in precise and unambiguous quantitative terms such as the percentage upward shift in threshold. Furthermore, the response from the patient is indicated in an earliest possible time. As comparision, the prior art relies qualitative and descriptive terms such as "a little better", "much better", etc. to communicate with the practitioner, resulting in drawbacks in three areas. Firstly, these terms are very subjective and different patient has his own feeling, degree of vagueness, and consistency in differentiating these relative levels. Consequently the information which the patient can communicate to the practitioner is subject to aberration and vacillation. There is high degree of vagueness in interpreting the result for the respective patient, and there is even higher vagueness in correlating the result of one object to those of the others. Secondly, it would take a considerable change in sensory threshold before the object can feel it without the help of the indicator stimulation provided by the present invention. Therefore response at a low level may escape attention. Thirdly, for the same reason, it would take a long time of treatment before a noticeable result.

The treatment-pattern programming 3-9 serves to control the application of the stimulations in a desired predetermined spatial and sequential fashion. It controls one or more of the following functions:
  a. The type of indicator stimulation to be used.
  b. The location of the indicator stimulation to be activated.
  c. The type of referencing stimulation to be used.
  d. The location of the referencing stimulation to be activated.
  e. The time sequence of occurrence of the indicator stimulation and the treatment stimulation.
  f. The spatial pattern of the indicator stimulation to be activated.
  g. The time seperation between successive groups of stimulations.
  h. The time duration for each group of the indicator stimulation and the treatment stimulation.
  i. The number of repeat cycles of the indicator stimulation and the treatment stimulation.

In many cases the object need repeated treatment or long period of treatment, there is a need for an individual unit of instrument for each individual object. In the prior art, such an individual unit is an identical type of that used in the clinic. The shortcomings in doing so have been discussed in the Background of Invention of this application.

One important improvement of the present invention is the departure from the prior art in this aspect. Instead of using the same type of instrument for both the clinical use and the individual use, a prescription-specific unit 3-11 catered to the individual requirement is provided to each object when needed. This individual unit 3-11 is of a different type from that used for the clinic. It has only a selected number of parameters and, selected number of controls from those available in the clinical unit. The selection is based on the diagnostic result using the clinical unit. Besides, the parameters adopted in the individual unit would in general have a range of values catered to the need of the object. The advantage of this part of the present invention has also been discussed in the section on Background of Invention on this application.

The prior-art applicator means 3-12 may be made of various material and in different sizes which is well known to persons skilled in the art. All these prior-art applicators have two drawbacks in common, i.e. the lack of mobility and the lack of partial selectivity, as discussed in the section on the Background of Invention of the present application.

The optional applicator means 3-13, 3-14, and 3-15 provide novel means to improve the mobility and partial selectivity when the stimulation is applied externally. They will be explained in detail in connection with FIGS. 7A, 7B, 8A, 8B and 8C.

FIG. 3 provides an overall outline on the improvements and novel features of the present invention over the prior art, i.e.
  a. Provides the method and implementation of novel optional parameters of subjective referencing stimulation, indicator stimulation, and the treatment-pattern programming of these two stimulations with the treatment stimulation.
  b. Provides improvement to the limitation of the prior-art by introducing a dual package instrumentation option.
  c. Provides improvement in the stimulation applicator means.

Figure 4A:
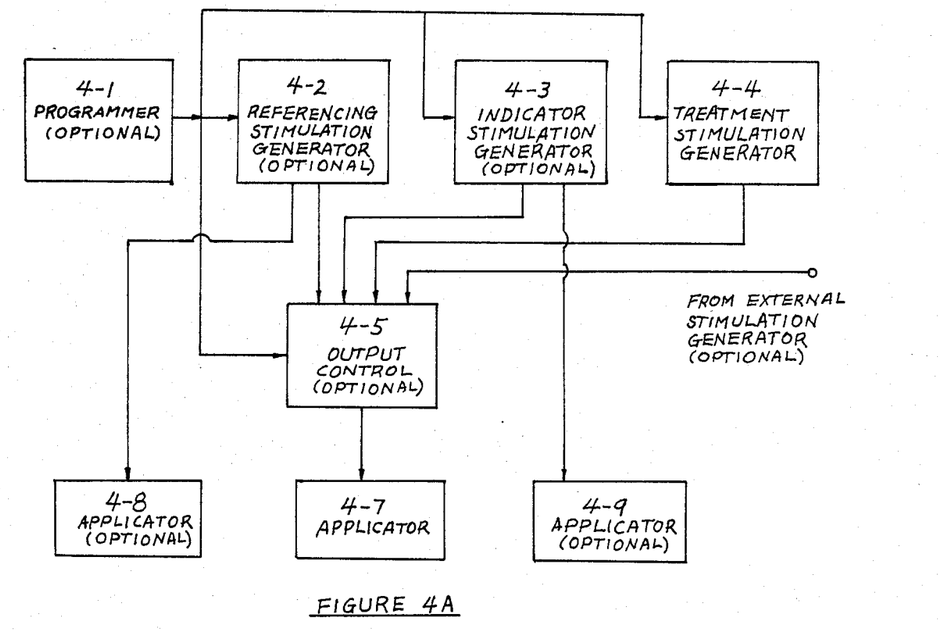
FIGS. 4A and 4B are block function diagrams showing by way of example instrumentation in support of the treatment procedure shown in FIG. 1.
Figure 4B:
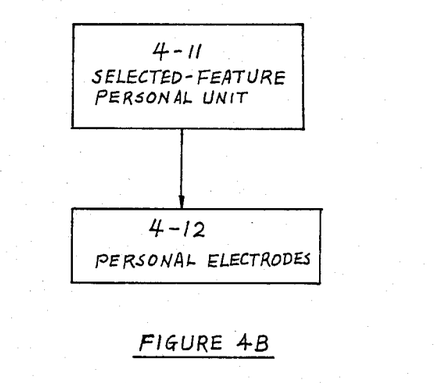

FIGS. 4A and 4B are block function diagrams showing by way of example a preferred embodiment of the instrumentation of the present invention. 4-1 is the treatment-pattern programming means which generates the functions listed in connection with 3-9. 4-2 is the referencing stimulation generating means which generates the functions listed in connection with 3-7. 4-3 is the indicator stimulating means which generates the functions listed in connection with 3-8. 4-4 is the treatment stimulation means which generates the functions listed in connection with 3-0. 4-5 is the output control means which has the following functions:
  a. Accepts the stimulations from the referencing stimulation generator 4-2, the indicator stimulation generator 4-3, and the treatment stimulation generator 4-4, and/or the external treatment stimulation generator 4-6.
  b. Controlled by the programming means 4-1 to distribute the various stimulations sequentially or concurrently to the one or more applicator means 4-7.

4-8 and 4-9 are optional applicator means directly fed from the respective referencing stimulation generator 4-2 and the indicator stimulation generator 4-3. It should be pointed out that in practical implementation of the various functions given in FIGS. 4A and 4B, some physical parts or electronic circuits may perform in more than one function.

FIG. 4B is the second part, or the individual treating unit of the instrumentation. 4-11 is the prescription-specific stimulation generating means which has the treatment parameters and respective ranges of values selected to the particular requirement of the object as result of the diagnostic procedure carried out using the first part of the instrumentation examplified in FIG. 4A. The referencing stimulation and/or the indicator stimulation may be included if required. 4-12 is the applicator means catered to the individual need of the patient. There is no limit to the number of units for the second part of the instrumentation. All patients treated with the first part may have an option to obtain a second part of the instrumentation catered to the individual need.

FIG. 5A is an example to illustrate the stimulating waveform at the output control means 4-5. 5-1$a$ depicts the first application of the referencing stimulation. It has an amplitude $h_{1a}$. 5-1$b$ depicts the second application of the referencing stimulation. It has an amplitude of $h_{1b}$ which makes the object barely respond to its presence and thus is regarded as thwe base level of the subjective reference of that object. In practice it may take several applications before the amplitude can be adjusted to the base threshold. The time separation $T_1$ between the two shots $h_{1a}$ and $h_{1b}$ is such that the object would be able to discriminate the separate existence of the two shots if both are above the threshold, and that any stimulating effect from the first pulse $h_{1a}$ would have been diminished to an insignificant level at the end of $T_1$. 5-2 is the indicator stimulation. It comes in groups of two or more pulses having a predetermined ratio of strength relative to each other. In the present example, the group has four pulses having respective amplitudes $h_2$, $h_3$, $h_4$, and $h_5$. The first pulse of the group is separation by a time interval $T_2$ from the referencing stimulus $h_{1b}$ so that the latter would have insignificant residue effect on the patient. Each pulse of the group is separation by a time interval $T_3$ which has the same requirement as $T_1$. In this example, the object would be able to respond the indicator stimulation as having only three pulses because the first pulse having an amplitude of $h_2$ which is below its responding level. However, it is able to respond the three pulses having amplitudes of $h_3$, $h_4$, and $h_5$ which are all above its responding threshold. During or after the treatment, if there is biological effect that changes the responding threshold, the object's response may have more counts or less counts to the group. For instance, the responding count would be two pulses if its threshold has been raised, and would be four if the threshold is lowered.

5-3 depicts the treatment stimulation. It occurs after a time period $T_4$ from the indicator stimulation and lasts for a period $T_5$ as determined by the operator. The strength, or dosage, of the treatment stimulation is calibrated against the referencing subjective base level of that object. Shown in figure is a ratio of $h_6:h_1$ which is less than unity and implies that the treatment stimulation is at a sub-basal level. The treatment stimulation may also be calibrated in the conventional way by scientific terms such as volt or milliampere if so desired.

At the end of the treatment stimulation, another group of indicator stimulation 5-4 is applied to check the effect of the treatment stimulation 5-3. The effect of the treatment stimulation can be interpreted in many ways depending on the experience of the practitioner and the type and location of the indicator stimulation. The treatment stimulation and the indicator stimulation may be applied alternately for any number of cycles to the satisfaction of the practitioner.

Other parameters may be also used in the referencing or indicator stimuli. FIG. 5B shows the examples in which frequency discrimination is used for referencing and indicating. 5-5 is a group of referencing stimulation. Each group has two or more pulses (there are three pulses in this example) having amplitudes above the detectible level and having a variable time seperation $T_7$ between pulses. The smallest value of $T_7$ that still enables the object to discriminate the pulses is the subjective base level of that object.

On the same basis, 5-6 depicts an example of the indicator stimulation. It comprises two or more groups of pulses in succession. The number of pulses in each group follows a predetermined pattern, i.e. the first group 5-6A consists of two pulses, the second group consists of three pulses, etc. The pulse separation within each group is constant but is varied in a predetermined pattern among the groups, i.e. the separation between pulses in the first group is $T_8$, the separation between pulses in the second group is $T_9$ which is a known fraction of $T_8$, and the separation between pulses in the third group is $T_{10}$ which is a known fraction of $T_9$. The amplitude and waveform of the indicator pulses are preferred to be the same as those of the referencing stimulation 5-5. By noting the the number of pulses which can be detected during and after treatment, it would enable the practitioner to determine whether the treatment has induced biological effect on the object. For instance, if it is detectible to a four-pulse group (5-6C) before treatment, but only a three-pulse group (5-6B) after treatment, then the practitioner would be safe to assume that the stimulation treatment has caused some biological effect on the object as witnessed from the change in his time-seperation discriminating power. It should be pointed out that the interpretation of the result from the use of the indicator stimulation is subject to the experience of the practitioner and his peers and is not part of the present invention.

Figure 6A:
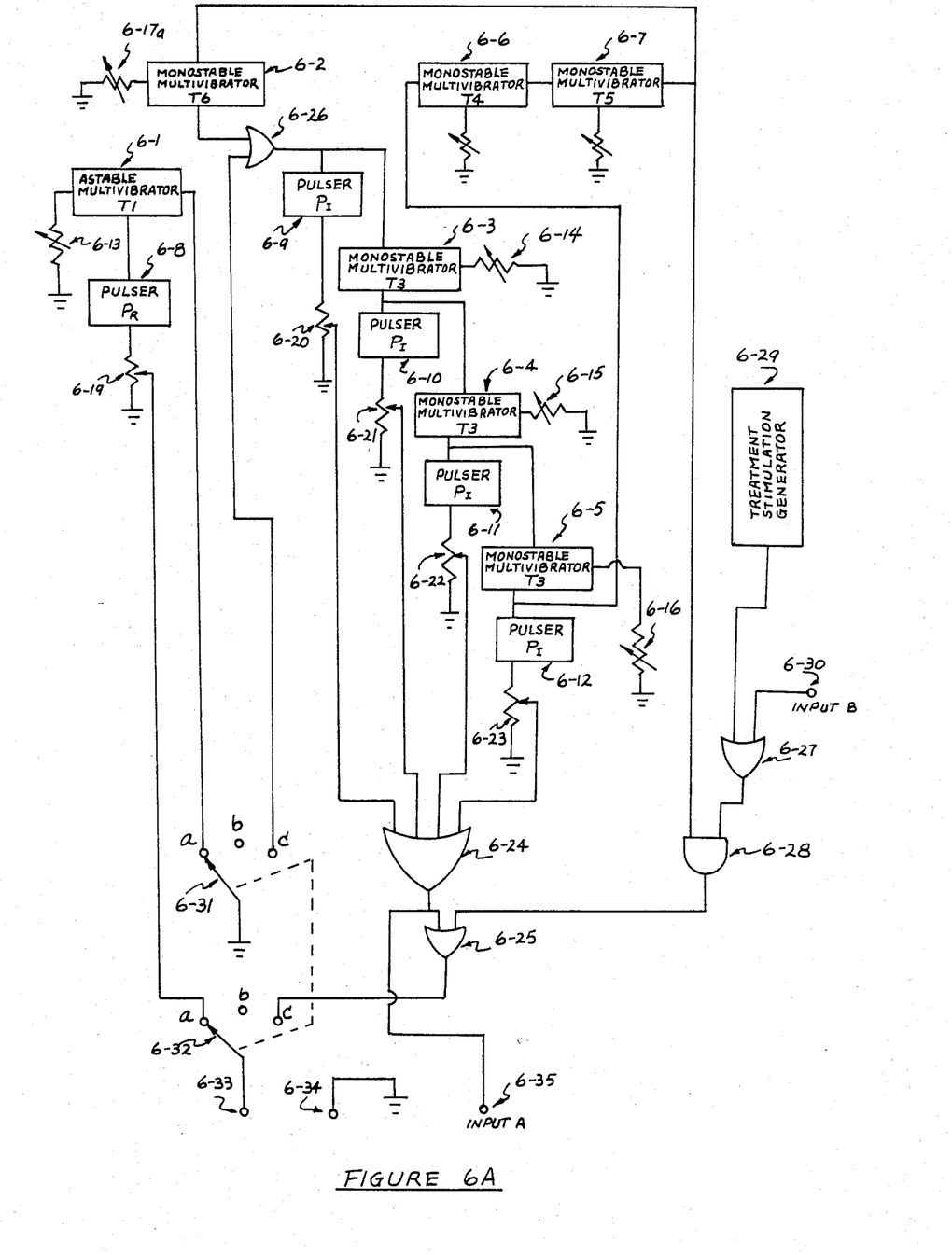
FIG. 6A shows by way of example the electric circuit capable of providing the novel function of the invention.

There is more than one way to implement the novel functions of the present invention into practice. As an example, FIG. 6A shows the electronic circuit for generating the exemplified waveform shown in FIG. 5A if electrical stimulation is employed. It should be pointed out that there could be other waveforms that can perform the functions of the present invention pending on the variation in requirements, and that for each waveform there could be more than one way to produce it.

In our example for electrical stimulation as shown in FIG. 6A, elementary electronic function blocks and necessary associated components are used and identified in the following:

6-1 is an astable multivibrator for generating the time base $T_1$ in FIG. 5A.

6-2 to 6-7 are monostable multivibrators for generating the time intervals as indicated in FIG. 6A which are respectively corresponding to that in FIG. 5A.

6-8 is a pulser for generating the referencing stimulation 5-1a, 5-1b, etc.

6-9 to 6-12 are pulses for generating the indicator pulses.

6-13 to 6-18 are variable resistors for controlling the time intervals generated from the respective multivibrators.

6-19 to 6-23 are potentiometers for varying the strength of the respective stimulating pulses 6-24 to 6-27 are logic gates which perform the "or" function.

6-28 is a logic gate which performs the "and" function.

6-29 represents the treatment stimulation generator 6-30 is connection to external treatment stimulation generator.

6-31 and 6-32 represent a double-pole, triple-position switch.

When in position "a", 6-31 turns on the astable multivibrator 6-1, and 6-32 connects the output of the referencing stimulation from the output taper 6-19 to the applicator 6-33.

When in position "b", the electronic system is disabled and the time during which the switch remains at position b determines the time interval $T_2$ as shown in FIG. 5A.

When in position "c", switch 6-31 initiates the pulser 6-9 and starts the subsequent indicator pulses and the treatment pulses. Switch 6-32 connects the applicator to the "or" gate 6-25 to tap on the indicator stimulation and the treatment stimulation.

6-33 and 6-34 are connectors to the applicator means.

When the monostable multivibrators and the pulsers are chosen to have the following characteristics:

a. To be triggered by a positive-to-ground voltage transition.

b. When triggered, the output voltage will go from ground level to a positive level for a period determined by their respective controlling variable resistors.

Figure 6B:
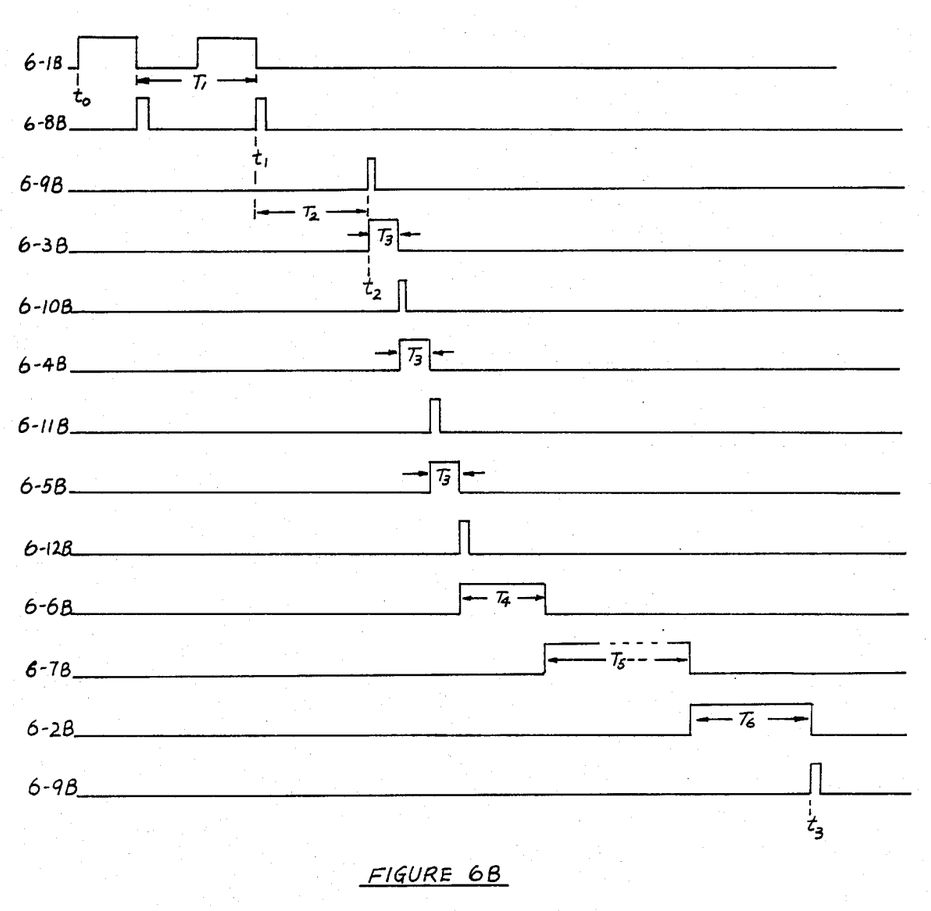
FIG. 6B shows the voltage waveform generated by the circuit of FIG. 6A.

Then the sequence of events of operation of the various components can be depicted in FIG. 6B in which, $t_0$ represents the time moment when the switch 6-31/6-32 is switched from the inactive position "b" to position "a".

$t_1$ represents the time moment when the switch 6-31/6-32 is switched from the referencing position "a" back to the inacting position "b" and stays there for the period $T_2$.

$t_2$ represents the time moment when the switch is switched to position "c" initiating the pulser 6-9 and starts the indicator-treatment stimulations cycle.

$t_3$ represents the time moment when the second cycle of the indicator-treatment stimulation cycle begins.

At the connectors 6-33 and 6-34, the applicator electrode receives a programmed stimulation waveform as shown in FIG. 5A and transmits the latter to the patient. The treatment waveform 5-3 is not shown, but is implied during the time period $T_5$.

Figure 7A:
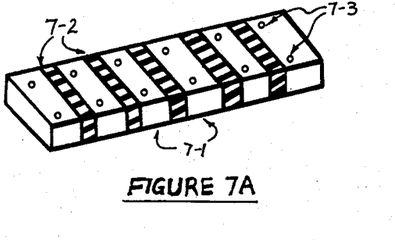
FIGS. 7A and 7B show by way of examples one form of a novel applicator electrode means of the present invention.
Figure 7B:
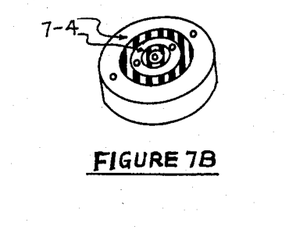

FIG. 7A shows by example a preferred embodiment of a part of the present invention on the improvement of the applicator means. This segment-select electrode comprises a plurality of conductive members 7-1, each having one or more connecting means 7-3, and proper number of insulating means 7-2 which renders the conductive member electrically isolated from one another except when connected by conducting wires at the connecting means 7-3. All the conducting members 7-1 and the insulating members 7-2 are mechanically linked to form a coherent single unit. The electrical stimulation is connected to whichever members of the conductive members through the connecting means 7-3 with conductive connectors. This arrangement allows the stimulation to be applied to a desired pattern within the coverage of electrode, leaving out the areas within the coverage where stimulation is not desirable. It also enables the three types of stimulation (referencing, indicator, and treatment stimulations) to be applied to separate areas within the general location covered by the electrode. The conductive members 7-1 may have any kind of functional geometry and be arranged in any compatible patterns. For example, FIG. 7B shows a segment-select electrode having its conductive member 7-5 in concentric annular segments.

Figure 8A:
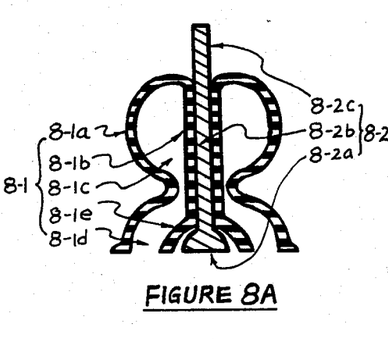
FIGS. 8A to 8C show by way of examples another form of novel applicator electrode means in cross-sectional views.

FIG. 8A shows by way of example a preferred embodiment of another version of improved applicator means which utilizes vacuum force for conveniently mounting the electrode onto the body of the treatment object and provide improvements over the prior-art similar devices. 8-1 is a slip-on vacuum assembly made of elastic material such as rubber. 8-2 is the slip-in electrode assembly tight fitted into the non-vacuum opening formed by the inner wall 8-1b of the vacuum assembly 8-1 and can be pushed downward if wanted. The upper portions of the outer wall 8-1a and inner wall 8-1b form the vacuum generating chamber 8-1c. Inner wall 8-1b itself forms a slip-on opening for the electrode 8-2 with the lower end of this opening 8-1e to allow the activating electrode surface 8-2a to come to contact with treatment object. The lower portions of the outer wall 8-1a and the inner wall 8-1b form the vacuum suction opening 8-1d. 8-2b is the slip-in member of the electrode 8-2. 8-2c is exposed portion of the electrode assembly for electrical connection and for receiving external force to move the electrode up or down with respect to the vacuum attaching assembly. Vacuum is generated by squeezing the vacuum chamber 8-1c and then release it. If the suction opening 8-1d is placed over the skin of the patient's body, the vacuum thus created will hold the electrode onto the skin. As time goes by, the vacuum diminishes due to leakage and the degree of contact pressure between the contacting interface 8-2a and the skin may also diminish, resulting in a decrease of efficiency. To remedy this, the electrode assembly 8-2 is pushed downward so that the interfacing pressure would remain the same as before.

Figure 8B:
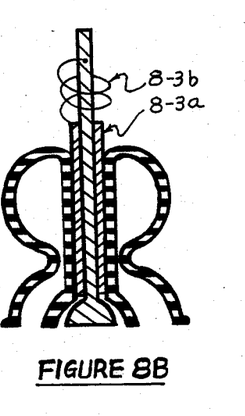

A more refined version of suctional electrode is shown in FIG. 8B. Added to the basic features as shown in FIG. 8A is a pressure generating means 8-3 comprising a motion guiding means 8-3a and a pressuring means 8-3b. In the example shown, the motion guiding means 8-3a employs a linear bearing. Its outside wall is fixed to the center opening of the suction cup. Its inside wall allows the electrode connector means 8-2b to slide axially with minimum friction. A pulling spring is used in this example as the pressuring means 8-3b. One end of the spring is attached to the motion guiding means 8-3a and the other end is attached to the electrode connecting means 8-2b, as shown in the drawing. This arrangement enables the contacting interface 8-2a to maintain a desired amount of pressure to the treatment object.

Figure 8C:
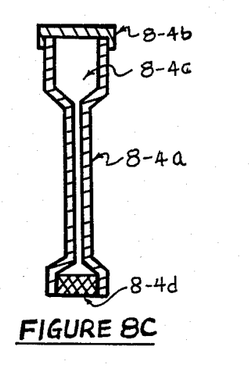

The suctional electrode may be refined further in many possible ways, for example its electrode assembly may have a self-contained electrolyte reservoir and feeding means 8-4 as shown in FIG. 8C. In this example, the electrode assembly 8-4 is made of a hollow structure having a connector means 8-4a, end covering 8-4b, reservoir and ducting 8-4c, and a porous electrode contacting interface 8-4d. Conductive electrolyte of the suitable kind is filled in the reservoir 8-4c and passes through the porous contacting interface 8-4d to keep the proper amount of electrolyte between the electrode and the skin to maintain the efficiency of electrical transmission.

The common features of the above versions of improved suctional electrodes are that the contacting pressure exerted by the activating surface of the electrode to the treatment object can be adjusted at will during the treatment operation for any desired pressure smaller than the negative pressure of the suction; that the electrode is outside of the vacuum chamber so that its change in vertical position and the amount of applied electrode jel will not effect the vacuum force. Prior art devices such as Phipps et al U.S. Pat. No. 3,534,733, or Thresher et al U.S. Pat. No. 2,600,175 do not have these desirable features.

A proper amount of coloring agent which is non-toxic to the skin, such as those used in cosmetic field or the food processing field, may be added to the conductive fluid to render the latter visible. This provides a visible record on the path of exploration when the practitioner probes along the patient's body to find the desirable location or locations for applying the stimulation. An example of such coloring agent is caramel. All forms of fluids and pastes which are capable of conducting electricity are regarded as electrolyte or conductive fluid in the above discussion.

FIGS. 9A, 9B, 9C and 9D serves to illustrate the relationship between the clinical unit and the individual unit of the instrumentation system of the present invention. Part 9A depicts, for illustration purpose, the parameters and their respective range of values in the clinical part of the instrumentation. The curves h—h', j—j', and k—k' respectively show the effectiveness of the parameters H, J, and K at their respective ranges of values. The vertical axes Nh, Nj, and Nk indicate the relative number of desirable or undesirable responses from the patient population, a positive value being indicative of desirable response while a negative value being indicative of undesirable response. The horizontal axes Mh, Mj, and Mk represent the values of the respective parameters H, J, and K. These curves are derived from prior experience and data. The ranges of values h1–h2, j1–j2, and k1–k2 are decided upon by the instrument designer when he intends to have the clinical unit applicable to a certain percentage, p, of the clinical cases expected, thus defining the capability and the parametric structure of the clinical unit.

Figure 9A:
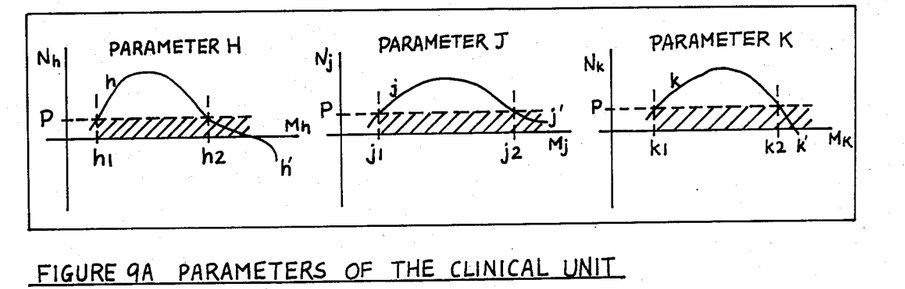
FIGS. 9A-9B illustrate the relationship between the clinical part and the individual part of the invention.
Figure 9B:
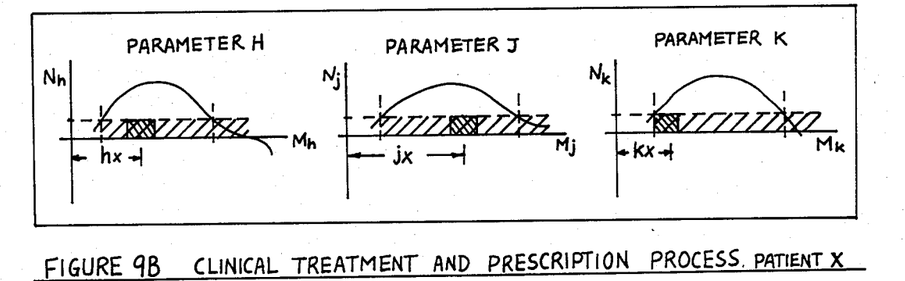

FIG. 9B depicts the clinical treatment and the prescription process for one individual patient. With a treatment procedure established by the treating person and with the help of accessories in the instrumentation, the set of optimum values of the parameters for inducing the desirable result to that patient would be determined. It is possible that the optimum value of one parameter may be dependent upon the the values of the others. In the figure, hx, jx, and kx are shown as the optimum values for the object X after at least one treatment with the clinical unit.

Figure 9C:
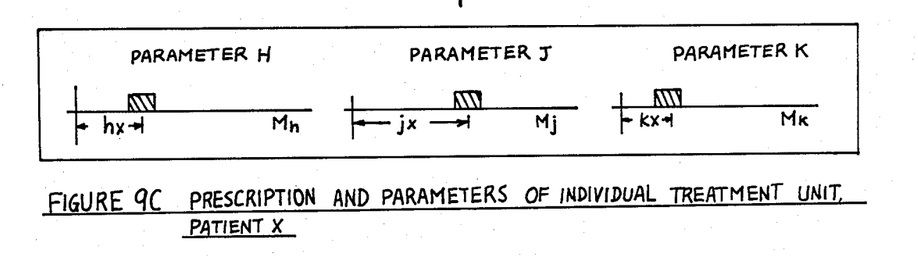

FIG. 9C depicts the prescriptional representation of the clinical treatment result. It defines the capability and the parametric structure of the individual unit of the instrumentation for the patient X. As far as patient X is concerned, the functional capability of the prescribed individual unit is as good as that from the clinical unit.

Figure 9D:
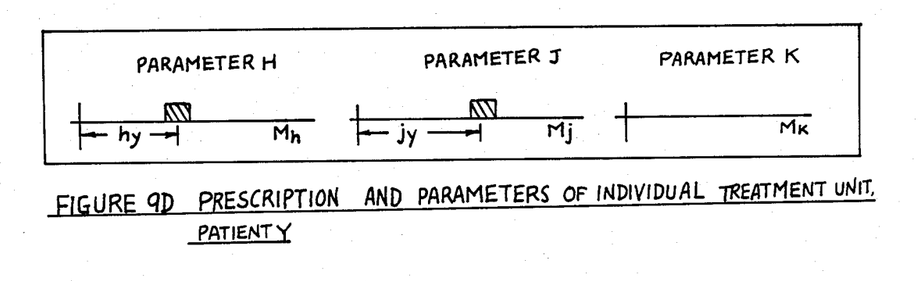

FIG. 9D depicts a similar prescriptional representation for another patient Y. It is illustrated there that patient Y does not have a desirable response from the parameter K and thus the latter needs not be incorporated into the individual treatment unit for patient Y.

In perspective, FIGS. 9A–9D shows the following relationship between the clinical part and the individual part of the instrumentation system of the present invention, i.e.

1. Geneologically, the individual treatment unit is created from the clinical unit through a treatment-prescription process. Without the clinical unit, there is no way to produce an individual treatment unit which has the equivalent capability of the clinical unit to one particular patient but is lower in cost, lighter to carry and simpler to operate.
2. Structurally, the two parts of the instrumentation system are intimately related in that the useful parameters in the individual unit belong to a sub-group of those of the clinical unit and the magnitude of the useful parameters belong to a sub-range of the magnitude of the respective parameters in the clinical unit.
3. Functionally, a synergistic relation exists between the two parts of the instrumentation system in that the clinical unit of the system serves as the source of creating the individual unit of the system, and the individual unit serves to compensate for the shortcomings of the clinical system for individual usage, so that the instrumentation system can read out for a better coverage of the patient population who are the potential beneficiaries, than otherwise possible. The following tabulation further illustrates this point,

| The clinical unit of the system |
| --- |
| Advantages: |
| comprehensive capability to provide intensive and broad coverage of cases of the object population, ability to explore in depth in one specific case the treatment requirements when exists. |
| Disadvantages: |
| bulky and expensive, many controls and adjustments, requires trained skill to operate, highly unlikely that any one patient would need all the capability. |

| The individual unit of the system |
| --- |
| Advantages: |
| equivalent capability as the clinical unit to the object to whom the individual unit is prescribed, convenient to carry and at lower cost, simpler operation which could be tailored to the operating ability of the object, the unit only need to carry whatever is needed by the object to whom the unit is prescribed. |
| Disadvantages: |
| none. |

While the invention which has been described in connection with a particular form, any one skilled in the art will have other modifications occur to him on the teaching of the present invention. These modifications are intended to be encompassed within the scope of the present invention.

I claim:

1. A method of applying stimulation to a biological body for a desired effect, comprising the steps of applying treatment from a clinical treating unit having a set of treatment parameters, of gauging the response from the treatment object, of selecting a subset of said of parameters which may induce the desirable effect to the said object, and of defining an individual treating unit having the said subset of parameters for the individual use of said object.

2. As in claim 1, therein exists in at least one parameter in the clinical treatment unit a range of variable magnitude, further comprising the step of selecting a sub-range from the said range of variable magnitude for the corresponding parameter in the said subset of parameters.

3. As in claim 1, further comprising the step of establishing a subjective reference by applying to the object groups of stimuli having a pre-determined number of repetitions and having at least one characteristic feature different from that of the other groups, detecting the number of response from the treatment object, and comparing the said number of response to the said pre-determined number of repetitions.

4. As in claim 1, comprising further the step of monitoring the effect of treatment by applying indicative measurement of response to the treatment object and detecting any change in the response of the said object during the treatment process.

5. In a stimulating system comprising a clinical treating unit having a set of treatment parameters, a method of defining an individual treating unit for a treatment object, comprising the steps of applying treatment from the said clinical unit to said object, of gauging the response from said object, and of selecting from said set of parameters a subset which may induce desirable effect to said object, and of including the said subset of parameters to the individual treating unit.

6. As in claim 5, therein at least one parameter in the clinical treating unit having a range of variable magnitude, further comprising the step of selecting a sub-range from the said range of magnitude for the corresponding parameter in the said subset of parameters.

7. In a stimulating system, the combination with a clinical unit having a set of treatment parameters, of an individual treating unit, comprising means to generate a subset of treatment parameters defined for a treatment object through a testing process, said subset of parameters being selected from the said set of parameters in the clinical unit, means to apply said subset of treatment parameters to said object, and means for supplying the operating energy for the generation of the said subset of parameters.

8. As in claim 7, therein exists for at least one parameter in the clinical treating unit a range of variable magnitude, further comprising means to control the magnitude of the corresponding parameter to be in a sub-range of magnitude prescribed for the said object.

9. In a stimulating system, the combination with an individual treating unit having a subset of parameters defined for an object, of a clinical treating unit comprising means to generate a set of treatment parameters from which to define through a testing procedure a subset of treating parameters to be incorporated in the said individual treating unit, means to select said parameters for said testing procedure, means to apply said parameters to the object being treated, and means to supply operating energy for generating said set of treatment parameters.

10. As in claim 9, further comprising means to control the magnitude of at least one of the parameters in the said set of parameters.

11. As in claim 9, further comprising means to generate a group of stimuli, which consists of a plurality of sub-groups each of which having at least one shot of stimulation and having at least one characteristic feature different from that of another sub-group.

12. A method of indicative measurement of response for a stimulation treatment to a biological body, comprising the steps of applying a group of stimuli to the object, said group consisting of a plurality of sub-groups each of which having at least one shot of stimulation and having at least one characteristic feature different from that of another sub-group, of obtaining from the object its response to each said sub-group, and of comparing the number of shots of stimuli to the number of response in each subgroup.

13. As in claim 12, wherein a different pre-determined number of stimuli is identified with a sub-group of stimulation having a different characteristic feature from those of other sub-groups.

14. As in claim 12, wherein the characteristic feature being the strength of the stimulation.

15. As in claim 12, wherein the characteristic feature being the duration of action of the stimulation.

16. As in claim 12, wherein the characteristic feature being the temporal separation between the action of the stimulation.

17. In an electrical stimulating system, the combination with a clinical treating unit having a set of treatment parameters, of an individual treating unit, comprising means to generate electrical stimulation having a subset of treatment parameters defined for a treatment object through a testing process, said subset of parameters being selected from the said set of parameters in the said clinical treating unit, and means to apply said stimulation to the object.

* * * * *